(12) United States Patent
Basu et al.

(10) Patent No.: US 7,835,486 B2
(45) Date of Patent: Nov. 16, 2010

(54) ACQUISITION AND RECONSTRUCTION OF PROJECTION DATA USING A STATIONARY CT GEOMETRY

(75) Inventors: Samit Kumar Basu, Niskayuna, NY (US); Bruno De Man, Clifton Park, NY (US); Jed Douglas Pack, Glenville, NY (US); Xiaoye Wu, Rexford, NY (US); Zhye Yin, Schenectady, NY (US); Peter Michael Edic, Albany, NY (US)

(73) Assignee: General Electric Company, Niskayuna, NY (US)

( * ) Notice: Subject to any disclaimer, the term of this patent is extended or adjusted under 35 U.S.C. 154(b) by 36 days.

(21) Appl. No.: 11/726,023

(22) Filed: Mar. 20, 2007

(65) Prior Publication Data

US 2008/0056435 A1 Mar. 6, 2008

Related U.S. Application Data

(60) Provisional application No. 60/841,010, filed on Aug. 30, 2006.

(51) Int. Cl.
*G01N 23/083* (2006.01)
(52) U.S. Cl. .............................. 378/9; 378/10
(58) Field of Classification Search ...... 378/9, 378/10, 19, 92, 98.6, 113, 124, 134
See application file for complete search history.

(56) References Cited

U.S. PATENT DOCUMENTS

| 2,340,500 | A | | 11/1942 | Zunick et al. |
|---|---|---|---|---|
| 4,057,725 | A | | 11/1977 | Wagner |
| 4,196,352 | A | | 4/1980 | Berninger et al. |
| 4,274,005 | A | * | 6/1981 | Yamamura et al. ............. 378/9 |
| 4,284,896 | A | | 8/1981 | Stonestrom |
| 4,384,359 | A | | 5/1983 | Franke |
| 4,547,892 | A | | 10/1985 | Richey et al. |
| 4,947,412 | A | | 8/1990 | Mattson |
| 4,965,726 | A | | 10/1990 | Heuscher et al. |
| 4,991,190 | A | | 2/1991 | Mori |
| 5,166,961 | A | | 11/1992 | Brunnett |
| 5,173,852 | A | | 12/1992 | Lonn |
| 5,175,754 | A | | 12/1992 | Casey et al. |

(Continued)

FOREIGN PATENT DOCUMENTS

EP    1277439 A1    1/2003

(Continued)

OTHER PUBLICATIONS

Lalush, David C., Feasibility of Transmission Micro-CT with Two Fan-Beam Sources, IEEE, pp. 1283-1286, Sep. 1-5, 2004, vol. 4, San Francisco, California.

(Continued)

*Primary Examiner*—Edward J Glick
*Assistant Examiner*—Thomas R Artman
(74) *Attorney, Agent, or Firm*—Fletcher Yoder

(57) ABSTRACT

Systems and methods are provided for acquiring and reconstructing projection data that is mathematically complete or sufficient using a computed tomography (CT) system having stationary distributed X-ray sources and detector arrays. In one embodiment, a distributed source is provided as arcuate segments offset in the X-Y plane and along the Z-axis.

18 Claims, 6 Drawing Sheets

U.S. PATENT DOCUMENTS

| | | | |
|---|---|---|---|
| 5,228,070 A | 7/1993 | Mattson | |
| 5,259,012 A | 11/1993 | Baker et al. | |
| 5,262,946 A | 11/1993 | Heuscher | |
| 5,268,955 A * | 12/1993 | Burke et al. | 378/135 |
| 5,276,614 A | 1/1994 | Heuscher | |
| 5,305,363 A | 4/1994 | Burke et al. | |
| 5,377,249 A | 12/1994 | Wiesent et al. | |
| 5,383,231 A | 1/1995 | Yamagishi | |
| 5,396,418 A | 3/1995 | Heuscher | |
| 5,412,562 A | 5/1995 | Nambu et al. | |
| 5,438,605 A | 8/1995 | Burke et al. | |
| 5,485,493 A * | 1/1996 | Heuscher et al. | 378/15 |
| 5,491,734 A | 2/1996 | Boyd et al. | |
| 5,544,212 A | 8/1996 | Heuscher | |
| 5,570,403 A | 10/1996 | Yamazaki et al. | |
| 5,633,906 A | 5/1997 | Hell et al. | |
| 5,654,995 A | 8/1997 | Flohr | |
| 5,682,414 A | 10/1997 | Saito | |
| 5,719,914 A | 2/1998 | Rand et al. | |
| 5,764,721 A | 6/1998 | Light et al. | |
| 5,848,117 A | 12/1998 | Urchuk et al. | |
| 5,960,056 A | 9/1999 | Lai | |
| 5,966,422 A | 10/1999 | Dafni et al. | |
| 6,002,738 A | 12/1999 | Cabral et al. | |
| 6,018,562 A | 1/2000 | Willson | |
| 6,047,040 A | 4/2000 | Hu et al. | |
| 6,125,167 A | 9/2000 | Morgan | |
| 6,130,929 A | 10/2000 | Saha | |
| 6,183,139 B1 | 2/2001 | Solomon et al. | |
| 6,208,711 B1 | 3/2001 | Rand et al. | |
| 6,229,870 B1 | 5/2001 | Morgan | |
| 6,233,308 B1 | 5/2001 | Hsieh et al. | |
| 6,236,705 B1 | 5/2001 | Stergiopoulos et al. | |
| 6,236,709 B1 | 5/2001 | Perry et al. | |
| 6,252,924 B1 | 6/2001 | Davantes et al. | |
| 6,256,369 B1 * | 7/2001 | Lai | 378/14 |
| 6,272,200 B1 | 8/2001 | Pan et al. | |
| 6,333,968 B1 | 12/2001 | Whitlock et al. | |
| 6,353,653 B1 | 3/2002 | Edic | |
| 6,385,282 B1 | 5/2002 | Francke et al. | |
| 6,385,292 B1 | 5/2002 | Dunham et al. | |
| 6,421,412 B1 | 7/2002 | Hsieh et al. | |
| 6,453,003 B1 | 9/2002 | Springer et al. | |
| 6,459,755 B1 | 10/2002 | Li | |
| 6,466,640 B1 | 10/2002 | Taguchi | |
| 6,507,639 B1 | 1/2003 | Popescu | |
| 6,522,712 B1 | 2/2003 | Yavuz et al. | |
| 6,529,574 B1 | 3/2003 | Hsieh | |
| 6,535,570 B2 | 3/2003 | Stergiopoulos et al. | |
| 6,674,837 B1 | 1/2004 | Taskar et al. | |
| 6,731,716 B2 | 5/2004 | Mihara et al. | |
| 6,735,271 B1 * | 5/2004 | Rand et al. | 378/4 |
| 6,754,300 B2 | 6/2004 | Hsieh et al. | |
| 6,760,399 B2 * | 7/2004 | Malamud | 378/9 |
| 6,795,521 B2 | 9/2004 | Hsu et al. | |
| 6,807,248 B2 * | 10/2004 | Mihara et al. | 378/10 |
| 6,901,131 B2 | 5/2005 | Edic et al. | |
| 6,914,959 B2 | 7/2005 | Bailey et al. | |
| 6,917,663 B2 | 7/2005 | Taguchi | |
| 6,934,357 B2 | 8/2005 | Boyd et al. | |
| 7,085,350 B2 * | 8/2006 | Dunham et al. | 378/119 |
| 7,085,352 B2 * | 8/2006 | Dunham | 378/122 |
| 7,103,137 B2 | 9/2006 | Seppi et al. | |
| 7,142,629 B2 | 11/2006 | Edic et al. | |
| 7,177,391 B2 | 2/2007 | Chapin et al. | |
| 7,233,644 B1 * | 6/2007 | Bendahan et al. | 378/57 |
| 7,280,631 B2 * | 10/2007 | De Man et al. | 378/10 |
| 7,324,623 B2 * | 1/2008 | Heuscher | 378/9 |
| 7,379,525 B2 | 5/2008 | Basu | |
| 7,706,499 B2 * | 4/2010 | Pack et al. | 378/9 |
| 2002/0025017 A1 | 2/2002 | Stergiopoulos et al. | |
| 2002/0074929 A1 | 6/2002 | Taskar et al. | |
| 2002/0085674 A1 | 7/2002 | Price et al. | |
| 2002/0094064 A1 | 7/2002 | Zhou et al. | |
| 2003/0043957 A1 | 3/2003 | Pelc | |
| 2003/0118155 A1 | 6/2003 | Ueno et al. | |
| 2004/0028177 A1 | 2/2004 | Pipino | |
| 2004/0114710 A1 | 6/2004 | Ozaki | |
| 2004/0136490 A1 | 7/2004 | Edic et al. | |
| 2004/0213378 A1 | 10/2004 | Zhou et al. | |
| 2005/0089134 A1 | 4/2005 | Bruder et al. | |
| 2005/0100126 A1 * | 5/2005 | Mistretta et al. | 378/15 |
| 2005/0111610 A1 | 5/2005 | De Man et al. | |
| 2005/0135550 A1 | 6/2005 | Man et al. | |
| 2005/0175143 A1 | 8/2005 | Miyazaki et al. | |
| 2005/0175151 A1 | 8/2005 | Dunham et al. | |
| 2005/0226364 A1 | 10/2005 | De Man et al. | |
| 2006/0002506 A1 | 1/2006 | Pelc | |
| 2007/0003004 A1 | 1/2007 | Delgado et al. | |
| 2007/0172024 A1 | 7/2007 | Morton | |
| 2008/0056436 A1 * | 3/2008 | Pack et al. | 378/10 |
| 2008/0056437 A1 * | 3/2008 | Pack et al. | 378/10 |

FOREIGN PATENT DOCUMENTS

WO    WO0267779 A1    6/2002

OTHER PUBLICATIONS

Hui Hu, Multi-slice Helical CT; Scan and Reconstruction; Jan. 1, 1999; vol. 26, No. 1; Medical Physics, AIP, Melville, NY, US.

* cited by examiner

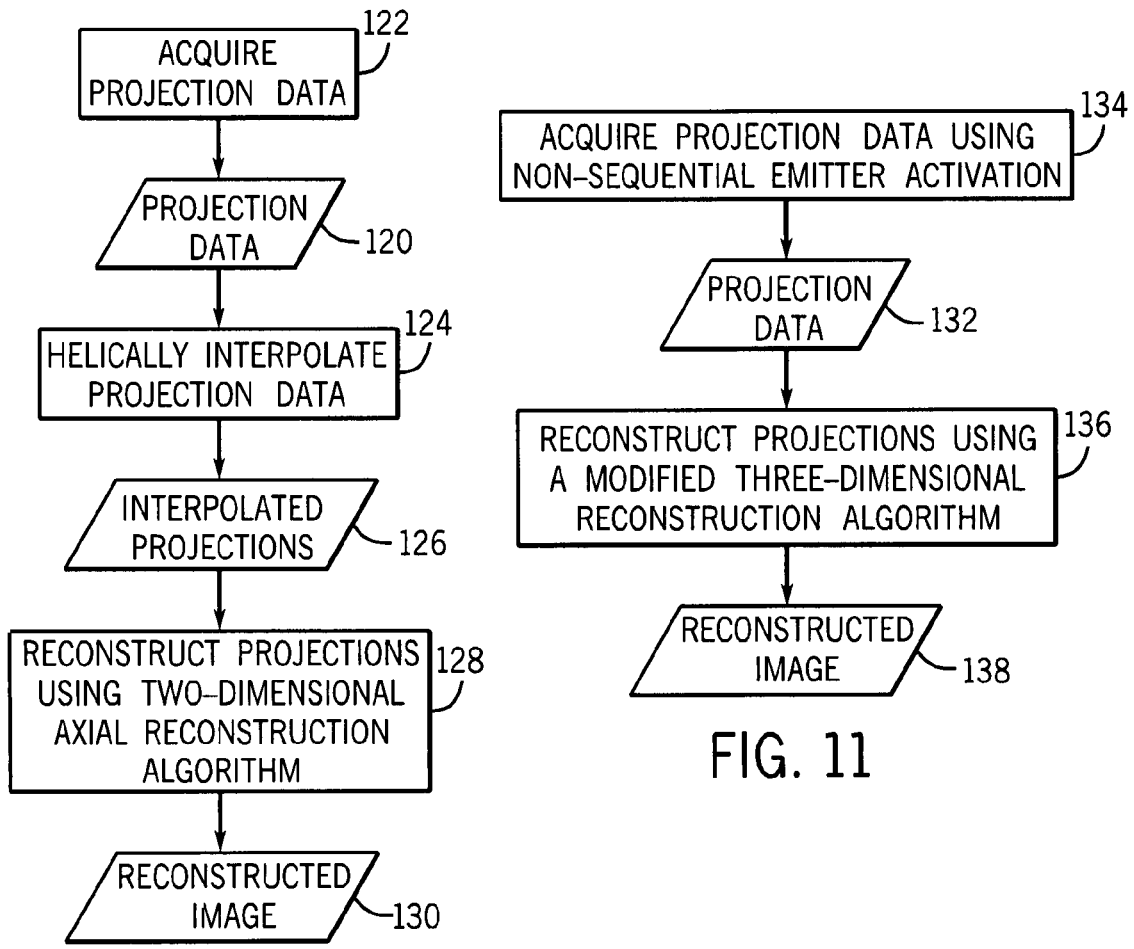

ACQUISITION AND RECONSTRUCTION OF PROJECTION DATA USING A STATIONARY CT GEOMETRY

CROSS REFERENCE TO RELATED APPLICATIONS

This application claim priority to U.S. Provisional Patent Application No. 60/841,010, entitled "Acquisition and Reconstruction of Projection Data Using a Stationary CT Geometry", filed Aug. 30, 2006, which is herein incorporated by reference in its entirety.

BACKGROUND

The present invention relates generally to the field of computed tomography (CT) imaging systems and specifically to source and detector configurations for stationary CT systems to facilitate measurement of more mathematically complete projection data for image reconstruction. A CT projection data set comprises projection measurements from a multitude of angular positions, or views, of the X-ray tube and detector relative to the patient or object being imaged. A set of mathematically complete projection data contains measurements that are sufficient to reconstruct the imaged volume without artifacts, within the constraints of the data acquisition system. Mathematical incompleteness can arise from a completely missing view of projection data, missing projection data within a portion of a view, or an inappropriate selection of geometrical imaging parameters such as the speed at which the patient or object traverses the gantry in a helical acquisition mode. It is essential that the projection data be mathematically complete, otherwise, it may be impossible to reconstruct image data with the fidelity required for a particular application.

Computed tomography is a technique which creates two-dimensional cross-sectional images or three-dimensional volumetric images of three-dimensional structures. Such tomographic techniques may be particularly useful for non-invasive imaging, such as for security screening, baggage and package examination, manufacturing quality control, and medical evaluation.

Conventional CT imaging systems may include a CT gantry and an examination table or conveyor for moving objects to be scanned into and out of the imaging volume defined by the X-ray collimators within the gantry. In such systems, the gantry is typically a moveable frame that contains an X-ray source, which is typically an X-ray tube including collimators and filters on one side, and detectors with an associated data acquisition system (DAS) on an opposite side. The gantry typically also includes rotational components requiring slip-ring systems and all associated electronics, such as gantry angulation motors and positioning laser lights.

For example, in so-called "third generation" CT systems the X-ray source and the detector array are in a fixed arrangement that is rotated by the gantry within an imaging plane and around the object to be imaged, so that the angle at which the X-rays intersect the object constantly changes. An X-ray detector may include a crystal or ionizing gas that, when struck by X-ray photons, produces light or electrical energy that may be detected and acquired for generation of the desired images. Such rotational CT systems have limitations regarding rotational speeds, mechanical balancing of the systems, and power and thermal requirements that become increasingly complex due to the need for rotationally compliant components. Further these limitations constrain the possible rotational speed of the gantry, making such rotational systems unsuitable for applications requiring good temporal resolution or high throughput.

Other types of CT architectures are non-rotational, i.e., stationary, and include configurations that offer high scanning speeds. For example, in one such stationary CT system, both the X-ray source and the detector are stationary and encircle the imaging volume. In such a system, the X-ray source may be a distributed X-ray source comprising many discrete electron emitters along its length and a distributed anode.

Since both the X-ray source and detector are stationary in such stationary CT configurations, they need to be designed to facilitate appropriate scanning protocols. For example, in one possible axial scanning configuration, the distributed X-ray sources at both longitudinal extents of a centered detector may be slightly offset (vertically and/or radially) relative to the area detector array. As a result, a volume in the center of the field of view of the imaging system is not subjected to X-rays, prohibiting reconstruction in this volume. Likewise, in a helical scanning configuration, a distributed X-ray source may be placed between two area detectors that circle the entire imaging volume. The X-rays are emitted through a gap between the two detector arrays to administer X-ray flux to the imaging volume. Because the X-ray source is also distributed around the entire bore of the gantry, the gap encircles the entire imaging volume, which prevents measurement of mathematically complete CT projection data and artifact-free image reconstruction of the volume. For example, for a helical acquisition, every reconstructed slice has some missing projection data. As a result, the acquired projection data is mathematically incomplete.

It is therefore desirable to provide improved source and detector configurations or modified data acquisition protocols for stationary CT systems to facilitate measurement of more mathematically complete data for image reconstruction and to provide suitable algorithms for reconstructing data acquired by such techniques.

BRIEF DESCRIPTION

An imaging system is provided. The imaging system includes two or more arcuate sources. Each arc source is configured to emit X-rays from a plurality of addressable locations. The imaging system also includes two or more detector arrays. The X-rays emitted by a respective arcuate source are generally incident upon at least one corresponding detector array.

A method for imaging a volume is provided. The method includes the act of activating a plurality of addressable X-ray source locations. Each X-ray source location is associated with a distributed arc source of a scanner. The scanner comprises two or more distributed arc sources. Projection data generated from measurements of X-rays emitted by the X-ray source locations when activated is acquired. Corresponding claims to tangible, machine-readable media comprising code executable to perform these acts are also provided.

DRAWINGS

These and other features, aspects, and advantages of the present invention will become better understood when the following detailed description is read with reference to the accompanying drawings in which like numerical labels represent like parts throughout the drawings, wherein:

FIG. 10 is a flowchart depicting exemplary logical steps for reconstructing projection data in accordance with embodiments of the invention; and FIG. 11 is a flowchart depicting exemplary logical steps for reconstructing projection data in accordance with embodiments of the invention.

DETAILED DESCRIPTION

Figure 1:
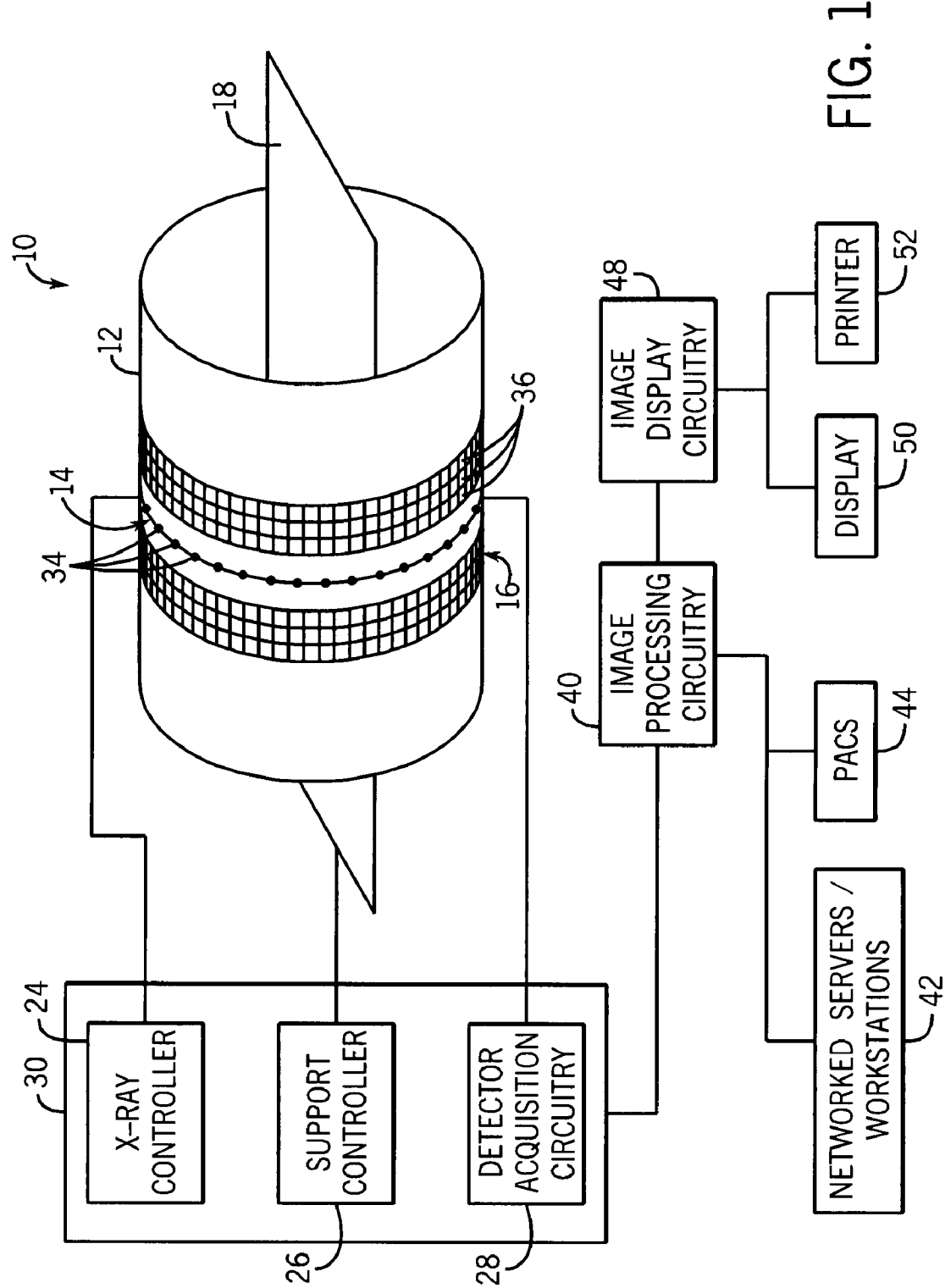
FIG. 1 is a diagrammatical representation of an exemplary stationary CT system in accordance with embodiments of the invention.

Referring to now FIG. 1, a computed tomography (CT) system is illustrated and designated generally by reference numeral 10. The CT system 10 comprises a scanner 12 formed as a cylindrical gantry and containing one or more stationary and distributed sources 14 of X-ray radiation and one or more stationary digital detector arrays 16, as described in greater detail below. The scanner 12 is configured to receive a support structure 18 passing through the imaging volume and upon which objects to be scanned are positioned. The support structure 18 can be moved through an aperture in the scanner 12 to appropriately position the object or objects in an imaging volume scanned during imaging sequences. In one embodiment, the support structure 18 is a conveyor belt configured to provide continuous or near-continuous movement of objects undergoing imaging through the scanner 12. In other embodiments, the support structure 18 is a table or support configured to move an object or patient into and within the scanner 12.

The system further includes a radiation source controller 24, a support controller 26 and data acquisition circuitry 28, some or all of which may function under the direction of a system controller 30. The radiation source controller 24 regulates timing for emissions of X-ray radiation from X-ray source locations 34 around the distributed X-ray source 14 toward a detector segment on an opposite side thereof, as discussed below. In an exemplary stationary CT implementation, the radiation source controller 24 may trigger one or more addressable electron emitters providing X-ray emission from source locations 34 of the distributed X-ray source 14 at specific intervals to facilitate multiple acquisitions of transmitted X-ray intensity data. In certain arrangements, for example, the radiation source controller 24 may addressably activate X-ray source locations 34 in sequences so as to collect adjacent or non-adjacent acquisitions of transmitted X-ray intensity around the scanner 12. Many such measurements may be collected in an imaging sequence, and detector acquisition circuitry 28, coupled to detector elements as described below, receives signals from the detector elements and processes the signals for storage and/or image reconstruction. In other configurations, the signals may be processed in real-time to generate reconstructions of the imaged object or objects within the imaging volume of the scanner 12. Support controller 26, then, serves to appropriately position the support structure 18 and objects to be imaged in a plane or volume in which the radiation is emitted. The support structure 18 may be displaced during or between imaging sequences, depending upon the imaging protocol employed.

System controller 30 generally regulates the operation of the radiation source controller 24, the support controller 26 and the detector acquisition circuitry 28. The system controller 30 may thus cause radiation source controller 24 to trigger emission of X-ray radiation, as well as to coordinate such emissions during imaging sequences defined by the system controller 30. The system controller 30 may also regulate movement of the support structure 18 in coordination with such emission so as to measure transmitted X-ray intensity data for different objects or volumes of interest or to achieve different modes of imaging, such as axial or helical modes. The system controller 30 also receives data acquired by detector acquisition circuitry 28 and coordinates storage, processing, and/or transmission of the acquired projection data. Although shown as components of the system controller 30 in FIG. 1, the radiation source controller 24, the support controller 26, and the detector acquisition circuitry 28 may or may not be provided within the same physical structure in an actual implementation.

It should be borne in mind that the controllers, and indeed various circuitry described herein, may be implemented as hardware circuitry, firmware and/or software. The particular protocols for imaging sequences, for example, will generally be defined by code executed by the system controller 30. Moreover, initial processing, conditioning, filtering, and other operations performed on the transmitted X-ray intensity data acquired by the scanner 12 may be performed in one or more of the components depicted in FIG. 1. For example, as described below, detector elements 36, provided in multiple rows and columns of the detector array 16, may produce analog signals representative of depletion of a charge in photodiodes such that the analog signals generally correspond to the X-ray energy incident on the respective detector elements 36 during a given sampling time. In one embodiment, the analog signals are converted to digital signals by electronics within the scanner 12 and are acquired by the detector acquisition circuitry 28. Partial processing may occur at this point, and the signals are ultimately transmitted to the system controller 30 for further filtering and processing in one such embodiment.

System controller 30 may also include or be coupled to an operator interface and to one or more memory devices. The operator interface may be integral with the system controller, and will generally include an operator workstation and/or keyboard for initiating imaging sequences, controlling such sequences, and manipulating data acquired during imaging sequences. The memory devices may be local to the imaging system 10 or may be partially or completely remote from the system 10. Thus, memory devices may include local, magnetic or optical memory, or local or remote repositories for imaged data for reconstruction. Moreover, the memory devices may be configured to receive raw, partially processed or fully processed data for reconstruction.

The imaging system 10 may include software, hardware, and/or firmware for image processing and reconstruction, depicted generally as image processing circuitry 40. The image processing circuitry 40 may be configured to communicate with or may be provided as part of the system controller 30. In addition, the image processing circuitry 40 may be configured to communicate with or be implemented as part of a connected local or remote system or workstation 42 or as part of a connected picture archive and communication system (PACS) 44 configured to store processed and/or unprocessed projection data. As will be appreciated by those skilled in the art, such image processing circuitry 40 may process the acquired CT projection data by various mathematical operations, algorithms and techniques. For example, conventional filtered back-projection techniques may be used to process and reconstruct data acquired by the imaging system 10. Other techniques, and techniques used in conjunction with filtered back-projection may also be employed.

In one embodiment, the imaging system 10 also includes image display circuitry 48 which may cause the display of the processed image data in electronic or printed form, such as on a display 50 or printer 52 respectively. As will be appreciated by those of ordinary skill in the art, such image display circuitry 48 may be implemented as software, hardware, and/or firmware and may be provided as part of the system controller 30, part of the operator interface, or as part of a connected workstation.

Figure 2:
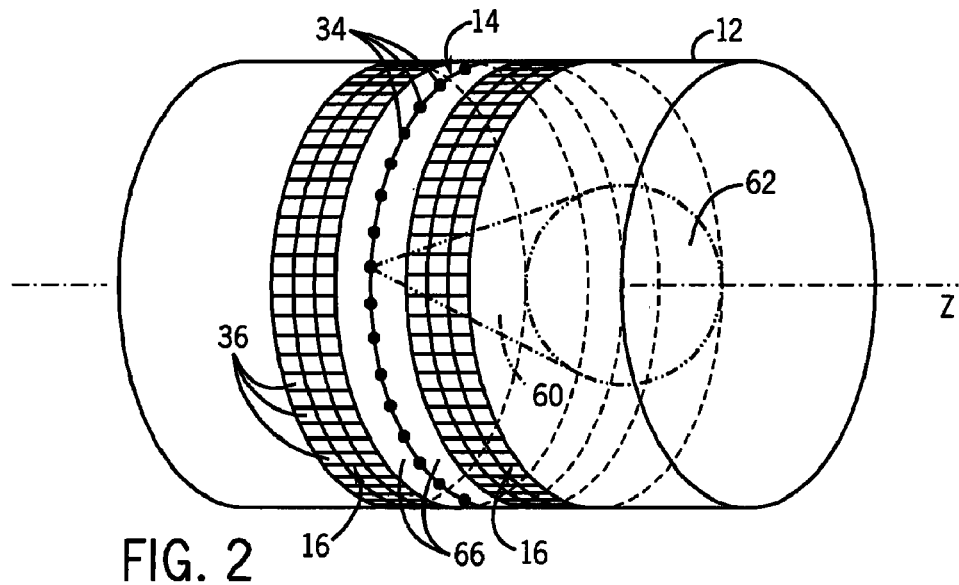
FIG. 2 is a diagrammatical representation of an exemplary source-detector configuration for use with a system of the type illustrated in FIG. 1.

The scanner 12 of stationary CT system 10 preferably includes one or more distributed X-ray sources 14 as well as one or more digital detectors 16 for receiving radiation and processing corresponding signals to produce projection data. FIG. 2 illustrates a portion of an exemplary scanner 12 defining an imaging volume having an axis, Z, along which an object or objects being imaged pass through or into the imaging volume. As shown in FIG. 2, in an exemplary implementation, the distributed X-ray source 14 may include a series of addressable X-ray source locations 34 that are coupled to radiation source controller 24 shown in FIG. 1, and which are triggered by the source controller 24 during operation of the scanner 12. In one embodiment, the addressable X-ray source locations 34 of the distributed source 14 are implemented using electron beam emitters that emit electron beams that are accelerated toward a target. The target, which may, for example, be a tungsten rail or element, emits X-ray radiation 60 upon impact of the electron beams thereon. The X-ray source may be operated in either reflection or transmission mode. In reflection mode, X-rays are meant to be produced primarily on the same side of the target as where the electrons impact. In transmission mode, X-rays are meant to be produced at the opposite side of the target from where the electron beam impacts the target. The X-ray beams may be collimated prior to entering the imaging volume such that the X-rays 60 are shaped into a desired cone, as depicted, fan, or other shape as they traverse the imaging volume.

While the above describes one possible implementation of a distributed X-ray source 14 having multiple addressable X-ray source locations 34, other implementations are also possible. For example, in one embodiment, a cold cathode emitter is envisaged which will be housed in a vacuum housing. A distributed stationary anode is then disposed in the housing and spaced apart from the emitter. Other materials, configurations, and principals of operations may, of course, be employed for the distributed source 14. For example, one emission device may be configured to transmit an electron beam to multiple locations on the target in order to produce multiple X-ray radiation beams. The emission devices may be one of many available electron emission devices, for example, thermionic emitters, cold-cathode emitters, carbon-based emitters, photo emitters, ferroelectric emitters, laser diodes, monolithic semiconductors, etc.

As described herein, the present stationary CT techniques are based upon use of a plurality of distributed and addressable electron emission sources for generation of a multitude of addressable, distributed X-ray source locations 34 along one or more sources of radiation 14. Moreover, each distributed source of radiation 14 may be associated in single unitary vacuum enclosure or in a plurality of vacuum enclosures designed to operate in cooperation. The individual X-ray source locations 34 are addressable independently and individually so that radiation can be triggered from each of the X-ray source locations 34 at points in time during the imaging sequence as defined by the imaging protocol. In other configurations, the X-ray source locations 34 are addressable in logical groups, for example pairs or triplets of X-ray source locations 34 may be activated together. Where desired, more than one such X-ray source location 34 may be triggered concurrently at any instant in time, or the X-ray source locations 34 may be triggered in specific sequences to mimic rotation about the imaging volume, or in any desired sequence around the imaging volume or plane.

Returning to FIG. 2, the addressable X-ray source locations 34 are positioned around the circumference of the imaging volume and, when activated, cause emission of X-rays 60 through the imaging volume onto a corresponding portion 62 of the detector array 16. Detector elements 36 in a portion of the detector array 16 upon which X-rays are incident produce a signal which may be read out by the detector acquisition circuitry 28 of FIG. 1. In one embodiment, the detector elements 36 include a scintillation-type device, a photodiode and associated thin-film transistors. X-ray radiation 60 impacting the detector elements 36 is converted to lower energy photons by a scintillator and these photons impact the photodiodes. A charge maintained across the photodiodes is thus depleted, and transistors may be controlled to recharge the photodiodes and thus measure the depletion of the charge. By sequentially measuring the charge depletion in the various photodiodes, each of which corresponds to a detector element 36 or pixel in the collected data for each acquisition, data is collected that encodes the energy of transmitted radiation through the object at each of the pixel locations. This acquired data may be processed to convert the analog signals to digital values, transformed to represent line integrals of linear attenuation coefficient, possibly filtered, and transmitted to image processing circuitry 40 of the imaging system 10 as described above. Although the detector arrays 16 have been described in terms of scintillator-based energy-integrating devices, other detector types such as gas-ionization, direct-conversion, photon-counting, or energy-discriminating detectors are equally suitable.

As depicted in FIG. 2, gaps 66 are provided between the distributed source 14 and the detector array 16 at interfaces. In particular, to allow suitable transmission of X-rays from X-ray source locations 34 of the distributed source 14, detector elements 36 are not present adjacent to the source 14, resulting in a gap 66 in the detector array 16 around the distributed source 14. Such gaps 66 may result in mathematically incomplete projection data being acquired during an imaging operation due to the absence of detector elements 36 in gap 66 and, therefore, may lead to image artifacts or to otherwise lower quality images being generated than is desired.

In one implementation, the individual activation sequence of the X-ray source locations 34 of the distributed source 14 is modified to increase the mathematical completeness of the projection data for objects passing through the imaging volume of the scanner 12 using the support structure 18. In particular, in one embodiment, the X-ray source locations 34 of the distributed source 14 are individually activated in a non-sequential pattern, i.e., an adjacent X-ray source location is not activated following activation of a first X-ray source location in the primary direction of activation. In one such embodiment, an activation pattern may be selected or configured such that the X-rays emitted by an activated X-ray source location 34 are not incident on a portion of the detector array 16 upon which X-rays emitted by the previous or subsequently activated X-ray source locations 34 are also incident.

In another embodiment, a first X-ray source location may be activated followed by the activation of a second X-ray source location that is displaced by some fixed angle, such as 90°, from the first X-ray source location in a counter-clockwise direction around the scanner 12. Subsequently, an X-ray source location adjacent to the first X-ray source location in the counter-clockwise direction is activated followed by an X-ray source location adjacent to the second X-ray source location in the counter-clockwise direction, and so forth. In this manner, denoting X-ray source locations in terms of angular locations about a circular scanner, one possible X-ray source location activation or triggering pattern may be: 0°, 90°, 1°, 91°, 2°, 92°, and so forth about the scanner 12. While the integer angular descriptions are provided here by way of example and to simplify explanation, one of ordinary skill in the art will appreciate that more than one X-ray source location 34 may be spaced between integer angular locations on a scanner 12, i.e., more than 360 X-ray source locations 34 may be provided on the distributed source 14. Further, angular offsets other than 90°, such as 45°, 120°, 60°, and so forth, may also be employed. Moreover, either a clockwise or counter-clockwise activation of the X-ray source locations 34 is conceived.

Figure 3:
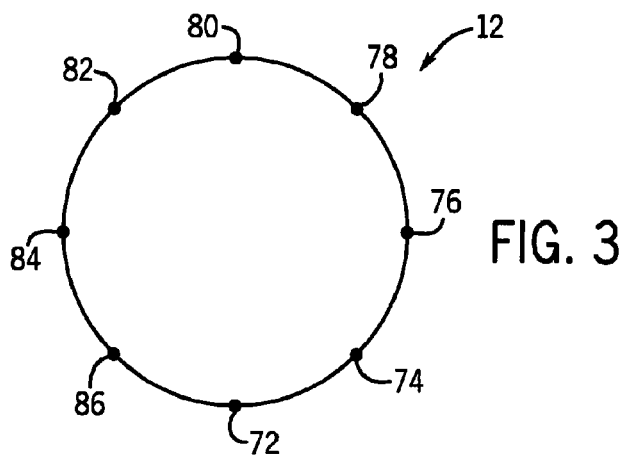
FIG. 3 is a diagrammatical representation of exemplary emission locations for the distributed source of FIG. 2.

Turning now to FIG. 3, a further embodiment of this technique is described in a simplified example in which only eight X-ray source locations 72, 74, 76, 78, 80, 82, 84, 86 are described. In this example, the X-ray source locations are separately activated in the following order:

| | |
|---|---|
| 1 | X-ray source location 72 |
| 2 | X-ray source location 76 |
| 3 | X-ray source location 74 |
| 4 | X-ray source location 78 |
| 5 | X-ray source location 76 |
| 6 | X-ray source location 80 |
| 7 | X-ray source location 78 |
| 8 | X-ray source location 82 |
| 9 | X-ray source location 80 |
| 10 | X-ray source location 84 |
| 11 | X-ray source location 82 |
| 12 | X-ray source location 86 |
| 13 | X-ray source location 84 |
| 14 | X-ray source location 72 |
| 15 | X-ray source location 86 |
| 16 | X-ray source location 74 | and so forth. As will be appreciated by those of ordinary skill in the art, hundreds of X-ray source locations 34 may actually be present on a distributed source 14; the present example is simplified and provided for illustrative purposes only. The type of activation pattern illustrated by the example is scalable and may be applied to scanners 12 having any number of X-ray source locations 34.

The types of activation patterns described above correspond to two helical scans acquired substantially simultaneously; other suitable non-sequential (or even random) activation patterns, allow the acquisition of projection data in an arbitrary manner and/or allow the projection data to be sampled along the surface defining the imaging volume, rather than only along one or more helical trajectories. In the present example, however, the projection data corresponding to the two helical scans is spatially interleaved and provides improved mathematical completeness of the acquired projection data for imaged objects passing through the image volume of the scanner 12 using the support structure 18. In particular, in these embodiments an X-ray source location 34 is in the same X-Y plane as the other X-ray source locations 34 but, due to the motion of the object using the support structure 18, effectively has a different position in the Z-direction relative to the other X-ray source locations 34. Due to the offset within the X-Y plane and to the displacement along the Z-axis, missing projection data can be compensated using the projection data that corresponds to the second helical projection data set. Typically the compensating ray originates from a source location 34 that is either in the same X-Y position as the unmeasured ray, as described above, or at the conjugate X-Y position, as will be appreciated by those of ordinary skill in the art.

For example, for projection data acquired using the techniques described above, projection data in one helical projection data set that is missing due to the presence of the gap 66 may be compensated for using projection data from the second helical projection data set. In particular, in one embodiment, for each X-ray source location 34 corresponding to missing projection data, the portion of the pi-segment of the first helix for which the X-ray source location will be projected into the gap 66 is determined. However, instead of backprojecting an interpolated value for these X-ray source locations, the missing projection data is backprojected for the location from the corresponding but offset X-ray source locations of the other helix.

In this manner, two, three, or, in general, n X-ray source locations 34 provide projections on the detector array 16 where the gap 66 is offset along the Z-axis compared with a first X-ray source location, allowing otherwise missing projection data to be utilized. In one embodiment, reconstruction can be performed as separate reconstructions wherein the "designation" (i.e., offset or original) of the two helices is switched. The two reconstructions can be averaged, which is equivalent to applying a voxel-dependent weight during backprojection. As will be appreciated by those of ordinary skill in the art, the offset between the two helices should be chosen to be such that the projected gap regions for each helix do not overlap with one another or minimally overlap.

Figure 4:
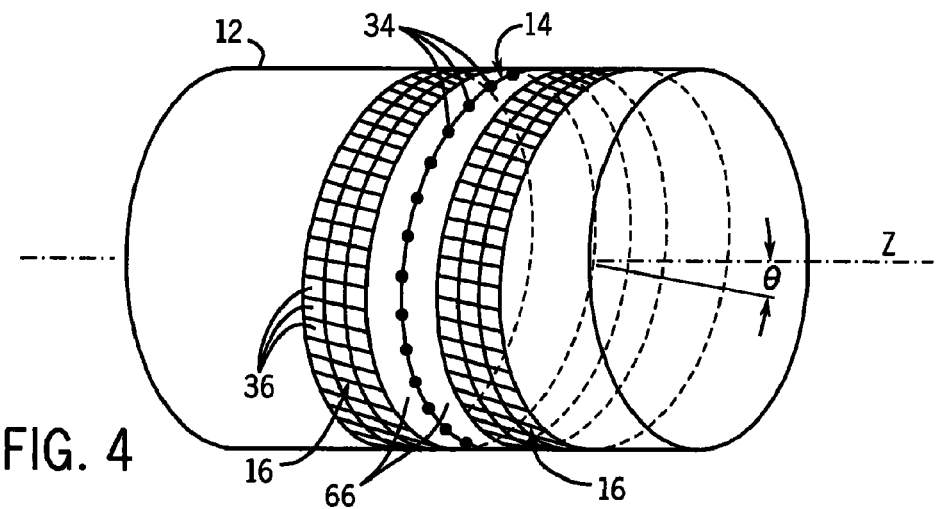
FIG. 4 is a diagrammatical representation of another exemplary source-detector configuration for use with the system of FIG. 1.
Figure 4A:
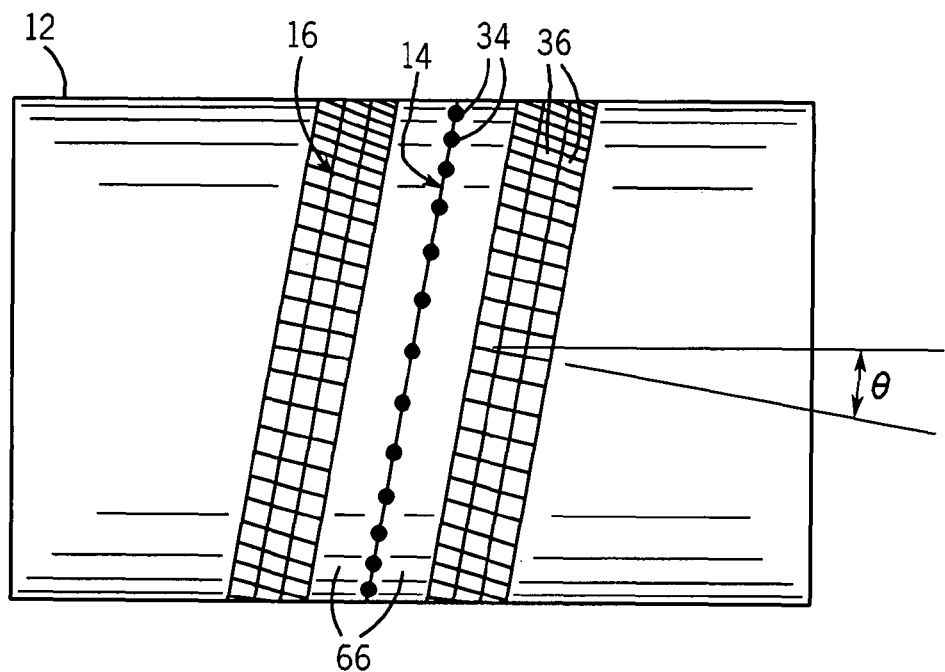
FIG. 4A is an elevation view of the exemplary source-detector configuration of FIG. 4.

Alternatively, turning now to FIGS. 4 and 4A, in another embodiment the distributed source 14, and possibly the detector array 16, are tilted relative to the main cylindrical axis of the scanner 12 by a tilt angle, θ, relative to the Z-axis of the scanner. As will be appreciated by those of ordinary skill in the art, in such embodiments the distributed source 14 may be elliptical or a tilted circle of a sufficient radius to acquire the required projection data. In such configurations, emitted rays may pass through the imaged region twice. By varying the tilt angle θ and the translation speed of the support structure 18, this redundancy can be optimized or increased. In this way, projection data, which would otherwise be missing due to the gap 66, may be compensated for or recovered. The vertical and horizontal boundaries of individual detector elements 36 may be oriented as shown in FIG. 4A, or they may be aligned with the axial and transaxial directions, respectively, as defined by the scanner geometry.

Figure 5A:
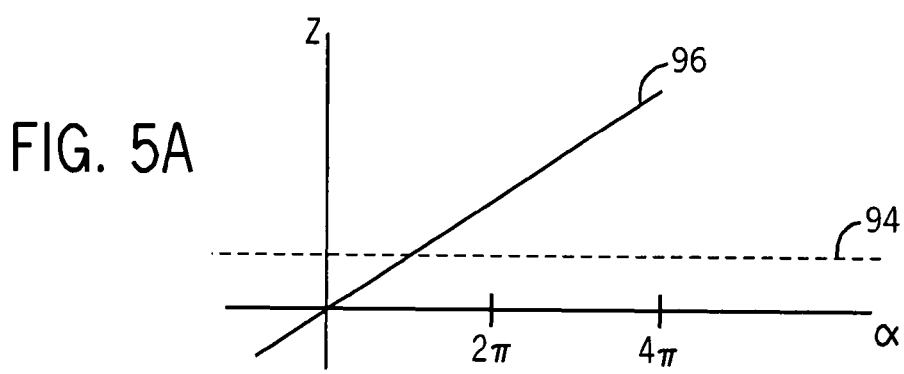
FIG. 5A is a graphical representation depicting source trajectory or object position for a non-tilted source-detector configuration.

For example, referring now to FIG. 5A, a plot of Z values versus rotational angle α is depicted for a conventional configuration of scanner 12 with no tilt of the distributed source 14, i.e., θ=0. Line 94 represents a given Z location. As an object traverses the scanner 12 by the support structure 18, depicted by the source trajectory line 96, data is acquired for each part of object along the helical source trajectory only once, resulting in missing data corresponding to the gap 66 in the detector array 16. The intersection of source trajectory line 96 and the Z position line 94 presents the angular position of the source when it passes through the given Z location. Only one such intersection point exists.

Figure 5B:
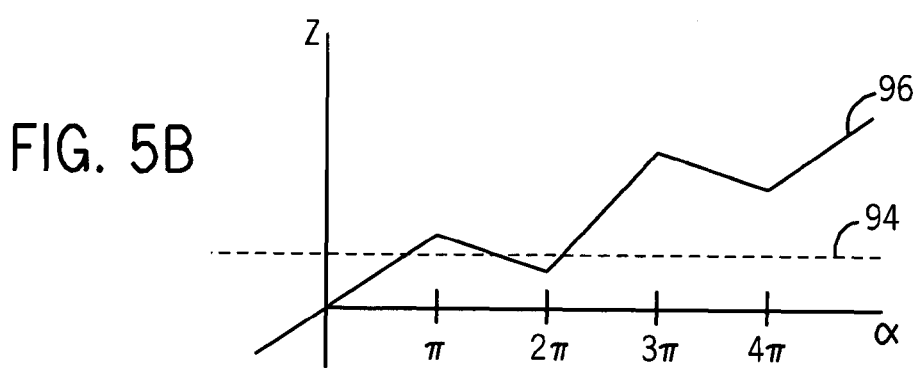
FIG. 5B is a graphical representation depicting source trajectory or object position for the tilted source-detector configuration of FIG. 4.

Referring now to FIG. 5B, a similar plot of Z values versus rotational angle α is depicted for a configuration of scanner 12 where the distributed source 14 is tilted relative to the Z-axis, i.e., θ≠0. In such an embodiment, there are multiple tilt rotational angles α for some Z values, as depicted by the intersection points of line 94 and line 96. As an object traverses the scanner 12 by the support structure 18, depicted by the source trajectory line 96, the resulting acquired data has some redundancy, which can be leveraged in the reconstruction process to compensate for mathematical incompleteness of the data. In effect, certain regions of a reconstruction slice can be augmented with the additional projection data so that mathematical completeness can be improved.

Figure 6:
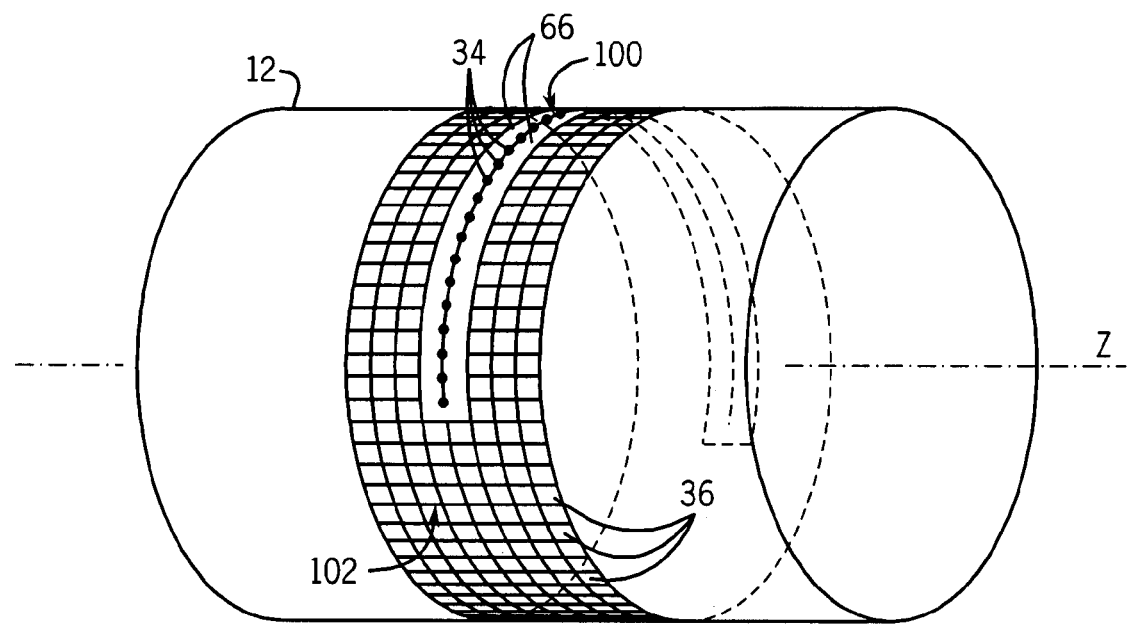
FIG. 6 is a diagrammatical representation of another exemplary source-detector configuration for use with the system of FIG. 1.
Figure 7:
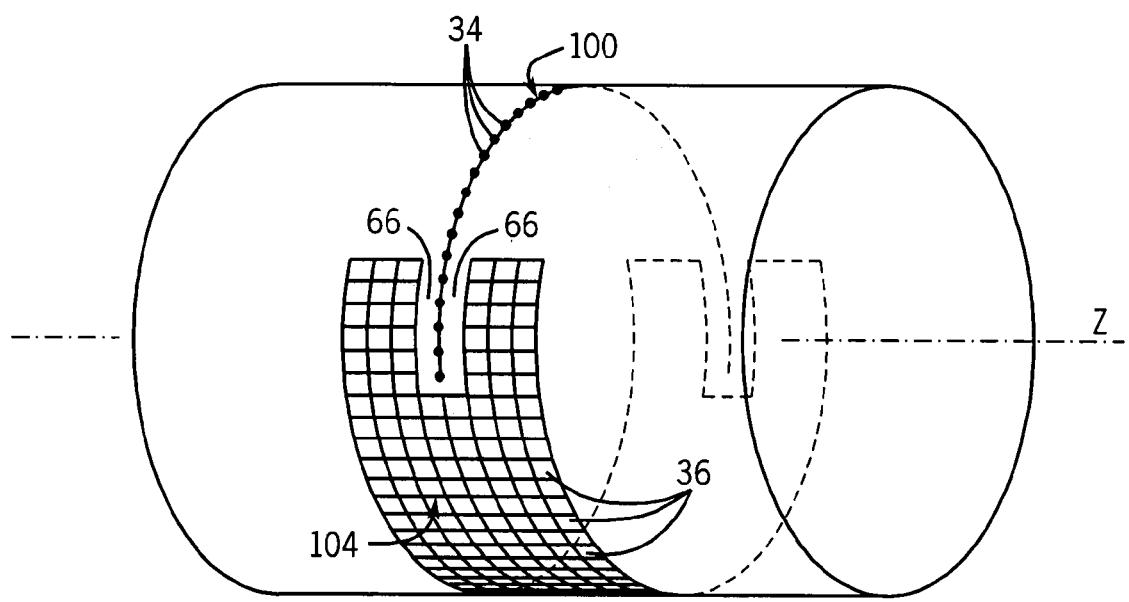
FIG. 7 is a diagrammatical representation of a further exemplary source-detector configuration for use with the system of FIG. 1.

Referring now to FIGS. 6 and 7, in another embodiment of the present technique, the distributed source 14 is provided as a U-shaped or generally semicircular source 100 having an angular span of approximately 180° or greater. For example, in one embodiment, the angular extent of the generally semicircular source 100 is 180° plus the fan angle of the emitted X-rays. In one implementation of such an embodiment, depicted in FIG. 6, a cylindrical-shaped detector array 102 is provided around the 360° span of the scanner 12. A gap 66 is provided in the detector array 102 to accommodate the generally semicircular distributed source 100 but is not present on those portions of the detector array 102 where no accommodation of the generally semicircular source 100 is needed. In another implementation of such an embodiment, depicted in FIG. 7, a partial detector array 104 is provided around a sufficient span of the scanner 12 to acquire projection data when the endpoint X-ray source locations 34 of the generally semicircular source 100 are active, i.e., the partial detector array 104 spans an angular range at least equivalent to the angular extent of the generally semicircular source 100 plus additional coverage to accommodate the fan angle of the emitted X-rays. A gap 66 is provided in the partial detector array 104 to accommodate the generally semicircular distributed source 100 but is not present on those portions of the partial detector array 104 where no accommodation of the generally semicircular source 100 is needed. In this manner, for both of the depicted embodiments of FIGS. 6 and 7, the detector gap 66 is eliminated over a large angular extent of the scanner 12, which improves the mathematical completeness of the acquired projection data.

With regard to the embodiments depicted in FIGS. 6 and 7, a complete set of projection data can be obtained under certain conditions. For example, if for every point in the field of view a subset of the X-ray source locations 34 form a dense sampling of a path, a respective point is projected onto the detector 102, 104 when each of these respective X-ray source locations 34 is activated, and the line segment connecting the endpoints of this path includes the respective point, a complete set of projection data may be obtained.

Furthermore, to the extent that redundant data is available using the described generally semicircular distributed source 100 configurations, the redundant data can be used to reduce noise in the reconstructed images. For example, noise reduction can be accomplished by combining reconstructions from data obtained on multiple (possibly overlapping) paths. As will be appreciated by those of ordinary skill in the art, the existence of such paths depends on the activation sequence for the X-ray source locations 34 on the generally semicircular distributed source 100. For example, specifically referring to FIGS. 6 and 7, multiple quasi-helical data acquisitions may be obtained by activating the X-ray source locations 34 sequentially from one end of the generally semicircular source 100 to the other. Furthermore, the pitch of the helices can be selected or modified by determining whether one or more of the X-ray source locations 34 are skipped in the activation sequence, such as by activating every other or every third X-ray source location 34 along the generally semicircular source 100 in sequence. In particular, by skipping X-ray source locations 34 in such an activation sequence, the effective pitch of the helix may be reduced. As the pitch is reduced, the density of relative locations at which projection data is acquired increases in the Z-direction of the partial cylinder on which all of the source locations lie. At the same time, the density of relative X-ray source locations in the transaxial direction, i.e., the X-Y plane, decreases.

With the foregoing in mind, helices and pitches may be configured such that for every plane passing through a reconstruction point an X-ray source location 34 is nearby. For example, a denser sampling may be desired in parts of the arc that are close to the edges of a non-circular reconstruction field of view. This may be accomplished by varying the number of X-ray source locations 34 that are skipped in the respective activation sequence. In this manner, a quasi-helical scan may be given variable pitch that provides complete projection data over the entire field of view or a portion of interest in the field of view. Similarly, by alternating between multiple X-ray source-location activation sequences, quasi-helical segments can be generated that overlap in their extent along the Z-axis.

Among the benefits of the embodiments depicted in FIGS. 6 and 7, is that, since the sampling is sparse in the transaxial direction and dense in the axial direction, the relative X-ray source locations can be considered as a two-dimensional sampling of a surface rather than as a set of one-dimensional samplings of individual helix segments. In addition, activation sequences can be designed and/or configured that jump between helix acquisitions to facilitate the acquisition of a complete set of projection data.

In another embodiment, mathematical completeness of projection data is improved by segmenting the distributed source 14 into multiple, possibly offset, segments. For example, referring now to FIG. 8, an embodiment is depicted in which the distributed source is provided as three distributed arc sources 110 offset in the Z-direction, each spanning a different angular region, such as 120°, of the scanner 12, though typically the distributed arc source 100 will span less than 180°. In the depicted example, each distributed arc source 110 spans different 120° regions of the total 360° defined by the scanner 12, though, as will be appreciated by those of ordinary skill in the art, the aggregate distributed arc sources 110 may actually span less than or greater than 360° if so desired. For example, in one embodiment, the aggregate distributed arc sources 110 may actually span 180° plus the fan angle of the emitted radiation 60. For this configuration, it is possible to acquire the requisite projection data using two or more arc sources 110.

Figure 8:
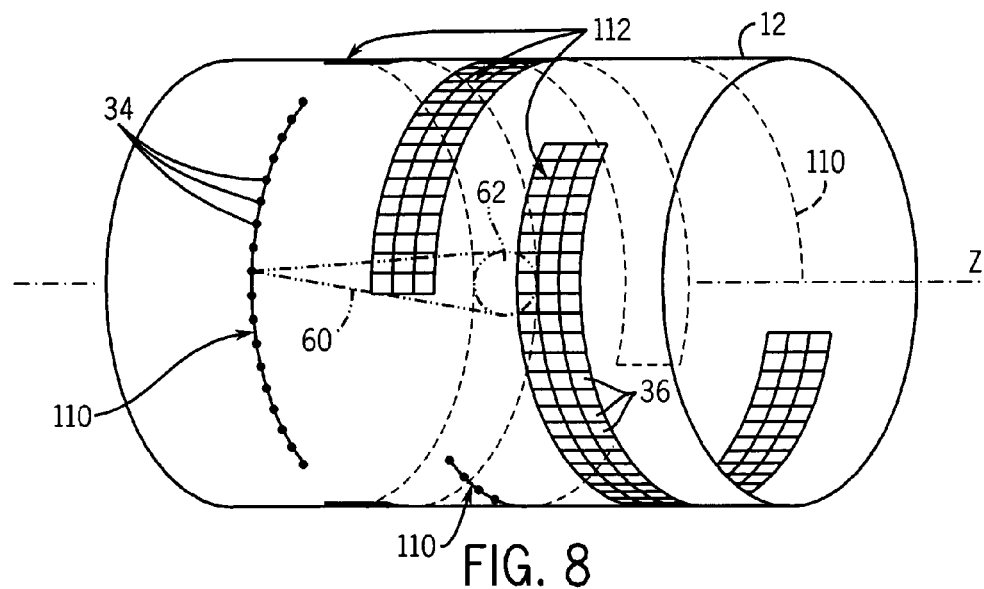
FIG. 8 is a diagrammatical representation of a further exemplary source-detector configuration for use with the system of FIG. 1.

In the depicted embodiment, the detector array 16 is also segmented such that a corresponding detector segment 112 is provided for each distributed arc source 110 on an opposing side of the scanner for the distributed arc sources 110. In the depicted embodiment, the detector segments 112 span a greater angular range than their corresponding distributed arc sources 110. In particular, the detector segments 112 are depicted as encompassing the angular range of the corresponding distributed arc source 110 plus whatever additional angular range is needed to allow for the fan angle of the emitted X-rays. In other words, in this embodiment, the angular extent of the detector segment 112 is equal to the angular extent of the distributed arc source 110 plus an extent to accommodate the fan angle of the X-rays emitted by the arc source 110. Since the relevant information that is measured is the collection of X-ray path integrals of the linear attenuation coefficient within the object being imaged, a detector section could be substituted by a source section and vice versa. As will be appreciated by those of ordinary skill in the art, such substitutions may depend on various system constraints, such as the relative cost of the distributed X-ray source and detector sections. In embodiments where the distributed arc source 110 spans less than 180° and the corresponding detector segment 112 does not overlap with the distributed arc source 110, as depicted in FIG. 8, the detector segment 112 can be constructed without a gap since the distributed arc source 110 does not need to be accommodated within the extent of the respective detector segment 112. Because there is not a gap in the detector segment 112, mathematically complete projection data is acquired by the detector segment 112. In other embodiments, detector segments 112 may simply be provided as detector rings with gaps provided for the distributed arc sources 110 but no gap opposite each respective arc source, thus allowing for improved data completeness.

As noted above and depicted in FIG. 8, the distributed arc sources 110 and detector segments 112 are offset in the Z-direction, i.e., the direction that objects are translated as they are being imaged, such as by support structure 18. In the depicted embodiment, the distributed arc sources 110 and detector segments 112 are offset such that they do not interfere with one another, i.e., X-rays emitted by a distributed arc source 110 are only incident on the corresponding detector segment 112, not on other detector segments. In an alternative embodiment, referring now to FIG. 9, the distributed arc sources 110 and detector segments 112 may be offset to a lesser extent in the Z-direction so that the detector segments 112 have regions that overlap or are contiguous. In such an implementation, projection data may be acquired from more than one detector segment 112 for some or all of the X-ray source locations 34 of the various distributed arc sources 110, however the distributed arc sources 110 still do not interfere with the detector segments 112, i.e., no gap is needed within the detector segments 112 to accommodate the distributed arc sources 110.

Figure 9:
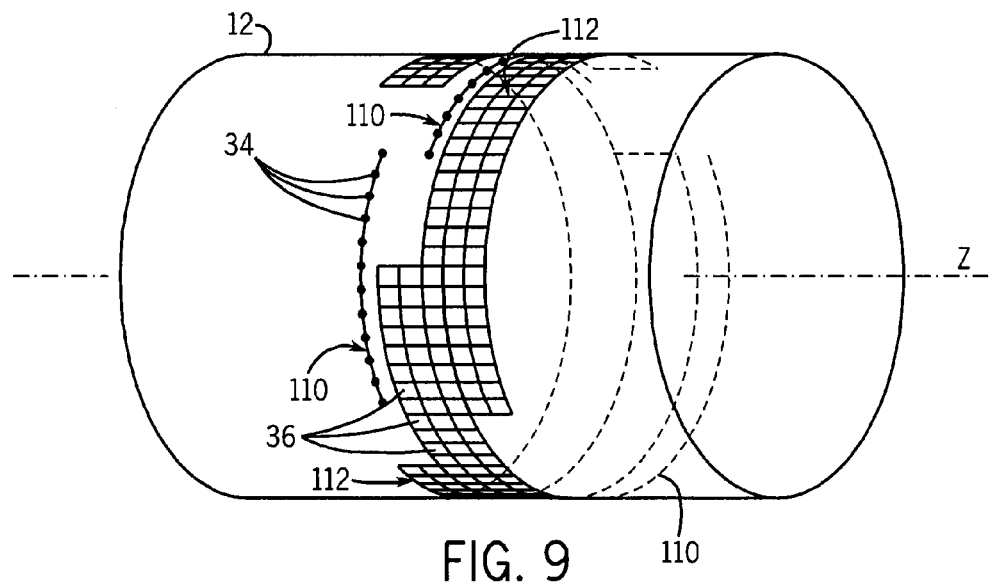
FIG. 9 is a diagrammatical representation of an additional exemplary source-detector configuration for use with the system of FIG. 1.

In one embodiment, the X-ray source locations 34 on the various distributed arc sources 110 of FIGS. 8 and 9 may be separately activated in a sequence or pattern that provides or approximates one or more offset helical scan configurations, i.e., helical projection data is acquired by the scanner 12 for objects passing through the imaging volume. For example, again describing X-ray source locations 34 on the scanner 12 in terms of angles for simplicity, an X-ray source location 34 at a 0° position on the scanner 12 might be initially activated followed by an X-ray source location 34 at 90°, an X-ray source location 34 at 180°, an X-ray source location 34 at 270°, an X-ray source location 34 at 1°, and X-ray source location 34 at 91°, and so forth. Angular offsets other than 90°, such as 45°, 120°, 60°, and so forth, may also be employed. As will be appreciated by those of ordinary skill in the art, such an activation sequence will acquire projection data corresponding to multiple helical trajectories that are spatially interleaved, i.e., interlaced, or spatially offset from one another. As will further be appreciated, the helical pitch and the spacing of the arc sources 110 in the Z-direction are related. If the arc sources 110 are not separated by a distance that equals the distance traversed during an integer number of helix turns, the given activation sequence (i.e., 0°, 90°, 180°, 270°, 1°, 91°, . . . ) will produce disjoint helical segments rather than a set of continuous helices. Therefore, in some embodiments, the arc source spacing is fixed to optimize detector usage (or any other desired factor). In such embodiments, after the arc source spacing is determined the helical pitch and the number of helices may be defined, and the corresponding firing sequence may be determined.

Furthermore, depending on the number of distributed arc sources 110 provided and the angular coverage of each arc source, consecutive X-ray source location activations may occasionally occur on the same distributed arc source 110 or may never occur on the same distributed arc source 110. As noted above, because there are no gaps in the respective detector segments 112, the acquired projection data is mathematically complete. Further, since the distributed arc sources 110 and the detector segments 112 can be staggered along the Z-axis of the imaging system, it is possible to simultaneously activate one or more X-ray source locations 34 on each of the distributed arc sources 110, i.e. locations at 1°, 91°, 181°, and 271° can be activated simultaneously as they do not emit X-rays which overlap with one another on the respective detector extents. The scanning procedures described above are such that projection data from multiple interlaced helices are acquired as the object traverses the imaging volume.

Other activation sequences may also be employed for the embodiments depicted in FIGS. 8 and 9. For example, an activation sequence emulating a conventional third-generation rotating CT system may be implemented. In such an implementation, an X-ray source location 34 at a 0° position on the scanner 12 might be initially activated followed by an X-ray source location 34 at 1°, an X-ray source location 34 at 2°, an X-ray source location at 3°, an X-ray source location 34 at 4°, and so forth. In this implementation, consecutive X-ray source location activations will generally occur on the same distributed arc source 110 except when transitioning to the next distributed arc source 110 when the angular extent of a distributed arc source 110 is reached. As previously noted, because there are no gaps in the respective detector segments 112, the acquired projection data is mathematically complete. Such a sequential scanning procedure allows the acquisition of a single helical projection data set. Moreover, since X-ray source locations 34 on each distributed arc source 110 are distributed, they can be activated in any desired sequence, even random sequences, to accomplish a specified imaging purpose. Such random or arbitrary activation sequence may allow the projection data to be sampled along the cylindrical surface defining the imaging volume, rather than only along one or more helical trajectories.

As will be appreciated by those of ordinary skill in the art, the configurations described above are contemplated for both axial, helical, or other appropriate scan modes. Depending upon the particular application, however, certain of the configurations may be better suited to one or more of these modes, such as to the axial mode for medical applications and helical modes for applications such as baggage scanning. Also the sources and detectors described in the above configurations may have different diameters, sizes, extents, and so forth. Moreover, the sources and detectors may be composed of linear sections, planar sections, or other spatially distributed sections, which approximate the configurations discussed above. Furthermore, other or related source and/or detector configurations may be employed using activation schemes as described above or to allow image data to be acquired as described above. Examples of such other source and/or detector configurations may be found in U.S. Patent Application Publication No. 2005/0111210, titled "Stationary Computed Tomography System and Method", published on May 26, 2005 and incorporated herein by reference in its entirety.

As would be appreciated by those skilled in the art, the configurations described herein overcome or otherwise compensate for the limitations of mathematically incomplete projection data measurement, such as in a helical scanning configuration of a stationary CT system. Specifically, in a helical scanning mode the limitation of mathematically incomplete projection data for an angular range of an effective source rotation is reduced or eliminated. This effect results in more mathematically complete projection data measurement for improved image quality in cone-beam reconstructions for stationary CT applications.

As will be appreciated by those of ordinary skill in the art, the preceding scanner configurations and X-ray source activation schemes allow, in some embodiments, for multiple sets of interlaced helical projection data to be acquired. Such interlaced helical projection data may present various reconstruction opportunities. For example, two reconstruction strategies are outlined in the exemplary logic set forth in FIGS. 10 and 11. Aspects of these strategies may be implemented, as appropriate, by the image processing circuitry 40 of FIG. 1. The exemplary reconstruction strategy of FIG. 10 relies on the use of parallel beam approximation and the use of a respective two-dimensional reconstruction algorithm while the exemplary reconstruction strategy of FIG. 11 utilizes a modified three-dimensional exact cone-beam reconstruction algorithm. As will be appreciated by those of ordinary skill in the art, other or related reconstruction techniques may be employed with the data acquired using the preceding scanner configurations and X-ray source activation schemes. Examples of such other reconstruction techniques may be found in U.S. Pat. No. 6,937,689, titled "Methods and Apparatus for Image Reconstruction in Distributed X-Ray Source CT Systems", issued on Aug. 30, 2005 and incorporated herein by reference in its entirety.

Turning now to FIG. 10, projection data 120 is initially acquired (Block 122). The projection data 120 may be an information dense projection dataset of multiple interlaced helices of projection data acquired by one or more of the techniques described above or by other techniques suitable for acquiring multiple interlaced helices of projection data. The projection data 120 is helically interpolated, i.e., approximated (Block 124) to generate a set of interpolated projections 126. As will be appreciated by those of ordinary skill in the art, the interpolation step 124 is an approximation that is suitable when the cone-angle of the system configuration is not too large. Typically such an approximation will be acceptable for cone-angles less than or equal to 2°. The interpolated projections 126 may then be reconstructed (Block 128) to generate a reconstructed image 130. The reconstruction step 128 may implement a suitable two-dimensional reconstruction algorithm, such as a two-dimensional axial reconstruction algorithm. Such two-dimensional reconstruction algorithms may be less computationally intensive than their three-dimensional equivalents and may, therefore, provide a very high reconstruction rate. If the cone-angle of the imaging system is still prohibitively large, it is possible to apply approximate or exact cone-beam reconstruction principles to reconstruct the volume.

In addition, the reconstruction scheme outlined in FIG. 10 allows for improved reliability of the CT imaging system 10. In particular, if a portion of the distributed source 14 or the detector array 16 (such as an arc source 110 or detector segment 112 of the scanner embodiment depicted in FIGS. 8 and 9) were to fail, the scanner 12 could be operated using short scan techniques, such as segment reconstruction techniques, requiring less than 360° of projection data for suitable image quality. Thus the system 10 can remain operational until the distributed source 14 or the detector array 16 can be repaired or replaced.

Turning now to FIG. 11, an alternative reconstruction technique is described. In this exemplary technique, the projection data 132 are acquired (Block 134) using a non-sequential activation sequence of the X-ray source locations 34 along the distributed source 14 (such as arc sources 110 of the scanner embodiment of FIGS. 8 and 9) resulting in a projection data set 132 that is sampled over the surface of the image volume rather than along a path. The non-sequential activation sequence for acquisition at step 134 may be accomplished by numbering the X-ray source locations 34, converting these numbers to binary, reversing the order of the bits, and activating the X-ray source locations 34 in the sequence of these modified numbers. Such an activation scheme is known as bit reversed firing (BRF). Alternatively, a fixed (typically small, i.e., less than 10) number of X-ray source locations 34 may be skipped between each activation. Such an activation scheme is known as super low pitch helical (SLPH) technique. In a further alternative, the angular position of each fired source location 34 (after the first) is determined by adding approximately $D(\sqrt{5}+1)/2$ degrees to the angular position of the previously fired source location 34 (where D is the total angular extent of an individual source arc in degrees). In instances where the resulting angle is greater than D, D may be subtracted from the angle such that the result is between 0 and D. Such an activation scheme is known as the Golden Ratio Firing (GRF) technique. Such a technique is easily implemented if the source locations 34 are equally spaced in angle and the number of source locations 34 in each arc source 110 or other distributed source 14 configuration is chosen from the Fibonacci sequence (i.e., 1, 1, 2, 3, 5, 8, 13, 21, 34, 55, and so forth). In this case, the number of source positions to advance is always equal to the previous number in the Fibonacci sequence. In other words, if we define $F_n$ to be the nth Fibonacci number and there are 377 (i.e., $F_{14}$) source locations 34 in each arc source 110, the index of the source position would be advanced by 233 (i.e., $F_{13}$) in each step. Since each Fibonacci number is the sum of the previous two, advancement in one direction by $F_{n-1}$ is equivalent to advancement by $F_{n-2}$ in the opposite direction when there are $F_n$ total source locations.

As will be appreciated by those of ordinary skill in the art, because the emission focal point, i.e., the activated X-ray source location 34, is moved about the surface defining the imaging volume, a surface is sampled rather than a path. Therefore, the projection data 132 can be reconstructed (Block 136) to generate a reconstructed image 138 using a three-dimensional cone-beam reconstruction algorithm that has been modified to accommodate the sampling scheme. For example, a reconstruction algorithm employed at Block 136 may be designed or configured to accommodate that the X-ray source locations 34 are sampled along the surface of a portion of a cylindrical surface rather than along a helical path.

One advantage of the scanning techniques described above with regard to FIGS. 10 and 11 is that in some scanner embodiments (such as those depicted in FIGS. 8 and 9) the longitudinal extent of the respective detector array 16 in the scanner 12 can be reduced roughly by the number of arc sources 110 since the arc sources 110 can operate simultaneously. For example, if a detector which is 60 cm in longitudinal length is needed for a third-generation configuration for a helical acquisition protocol and 4 arc sources 110 are included in a comparable stationary configuration, the longitudinal extent of the detector segments 112 could be reduced to 15 cm, i.e., reduced by a factor of 4. As will be appreciated by those of ordinary skill in the art, other scanner geometry considerations, throughput parameters, and scanner and imaging protocol factors may also affect the degree to which detector extent can be reduced. In embodiments where detector extent is reduced, scatter is also reduced due to the reduced detector extent.

As will be appreciated by those skilled in the art, the scanner geometries and reconstruction techniques described herein overcome or otherwise compensate for the limitations of mathematically incomplete projection data measurement, such as in a helical scanning configuration of a stationary CT system. Specifically, in helical scanning mode the limitation of incomplete projection data for an angular range of an effective source rotation is reduced or eliminated. This effect results in measurement of more mathematically complete projection data, which can be reconstructed by the techniques described herein for improved image quality.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An imaging system comprising:
two or more arcuate sources, each being configured to emit X-rays from a plurality of addressable locations; and
two or more detector arrays, the detector arrays being displaced relative to one another along the Z-axis of the imaging system wherein the X-rays emitted by a respective arcuate source are generally incident upon at least one corresponding detector array, and wherein the two or more arcuate sources are configured to be activated such that a plurality of subsets of projection data are generated that are combinable into two or more sets of interlaced helical projection data.

2. The imaging system of claim 1, wherein the combined angular length of the two or more arcuate sources is at least 180 degrees plus the fan angle of the X-ray beam.

3. The imaging system of claim 1, wherein each detector array has an arc length of at least the arc length of the corresponding arcuate source and an additional length to accommodate the fan angle associated with the X-rays emitted by the corresponding arcuate source.

4. The imaging system of claim 1, wherein the two or more arcuate sources are displaced relative to one another along an imaging volume axis along which one or more objects to be imaged are translated.

5. The imaging system of claim 1, wherein the two or more arcuate sources are displaced relative to one another within a plane orthogonal to an imaging volume axis of the scanner.

6. A method for imaging a volume, comprising:
activating a plurality of addressable X-ray source locations, wherein each X-ray source location is associated with a distributed continuous arc source of a scanner and wherein the scanner comprises two or more distributed continuous arc sources; and
acquiring projection data generated from measurements of X-rays emitted by the X-ray source locations when activated by two or more detector arrays, wherein the plurality of addressable X-ray source locations are activated such that the acquired projection data from each of the distributed continuous arc sources comprises a subset of projection data representing one or more incomplete helical turns about an imaging volume, wherein the subsets are combinable into two or more substantially mathematically complete sets of interlaced helical projection data.

7. The method of claim 6, wherein the two or more distributed continuous arc sources are displaced relative to one another along an imaging volume axis of the scanner.

8. The method of claim 6, wherein the two or more distributed continuous arc sources are displaced relative to one another within a plane orthogonal to an imaging volume axis of the scanner.

9. The method of claim 6, comprising translating one or more objects through the imaging volume of the scanner during the steps of activating and acquiring.

10. The method of claim 6, wherein said activating the plurality of addressable X-ray source locations comprises sequentially activating consecutive X-ray source locations around a circumference of the scanner.

11. The method of claim 6, wherein said activating the plurality of addressable X-ray source locations comprises non-sequentially activating consecutive X-ray source locations around the circumference of the scanner.

12. The method of claim 6, wherein said activating the plurality of addressable X-ray source locations comprises simultaneously activating two or more X-ray source locations, wherein the X-rays emitted by simultaneously activating the X-ray source locations do not overlap on one or more respective detector arrays.

13. The method of claim 6, wherein said activating the plurality of addressable X-ray source locations comprises activating the X-ray source locations in a random order to sample the surface of the imaging volume.

14. One or more tangible, machine-readable media, comprising code executable to perform the acts of:
activating a plurality of addressable X-ray source locations each being associated with a distributed continuous arc source of a scanner and wherein the scanner comprises two or more distributed continuous arc sources; and
acquiring projection data generated from measurements of X-rays emitted by the X-ray source locations when activated by two or more detector arrays, wherein the act of activating the plurality of addressable X-ray source locations activates the plurality of addressable X-ray source locations such that the acquired projection data from each of the distributed continuous arc sources comprises a subset of projection data representing one or more incomplete helical turns about an imaging volume, wherein the subsets are combinable into two or more substantially mathematically complete sets of interlaced helical projection data.

15. The one or more tangible, machine-readable media of claim 14 wherein the code executable to perform the act of activating the plurality of addressable X-ray source locations sequentially activates consecutive X-ray source locations around a circumference of the scanner.

16. The one or more tangible, machine-readable media of claim 14 wherein the code executable to perform the act of activating the plurality of addressable X-ray source locations non-sequentially activates consecutive X-ray source locations around a circumference of the scanner.

17. The one or more tangible, machine-readable media of claim 14 wherein the code executable to perform the act of activating the plurality of addressable X-ray source locations simultaneously activates two or more X-ray source locations, wherein the X-rays emitted by simultaneously activating the X-ray source locations do not overlap on one or more respective detector arrays.

18. The one or more tangible, machine-readable media of claim 14 wherein the code executable to perform the act of activating the plurality of addressable X-ray source locations activates the X-ray source locations in a random order to sample the surface of the imaging volume.

* * * * *